(12) United States Patent
Nakagawa

(10) Patent No.: US 7,997,900 B2
(45) Date of Patent: Aug. 16, 2011

(54) PARTIAL DENTURE

(76) Inventor: Hideo Nakagawa, Kashiba (JP)

( * ) Notice: Subject to any disclaimer, the term of this patent is extended or adjusted under 35 U.S.C. 154(b) by 0 days.

(21) Appl. No.: 11/921,679

(22) PCT Filed: Jun. 9, 2005

(86) PCT No.: PCT/JP2005/010560
§ 371 (c)(1),
(2), (4) Date: Dec. 6, 2007

(87) PCT Pub. No.: WO2006/131969
PCT Pub. Date: Dec. 14, 2006

(65) Prior Publication Data
US 2009/0047627 A1     Feb. 19, 2009

(51) Int. Cl.
*A61C 13/12* (2006.01)
(52) U.S. Cl. ........................................... 433/178
(58) Field of Classification Search .................. 433/172, 433/177, 178, 191, 193, 194, 180, 181, 182, 433/183
See application file for complete search history.

(56) References Cited

U.S. PATENT DOCUMENTS

| | | | | |
|---|---|---|---|---|
| 1,412,224 A * | 4/1922 | Williams | ..................... | 433/178 |
| 3,047,952 A * | 8/1962 | Yamamoto | ................... | 433/178 |
| 3,153,855 A * | 10/1964 | Holland | ..................... | 433/202.1 |
| 3,436,825 A * | 4/1969 | Oddo, Jr. | ..................... | 433/178 |
| 3,545,083 A * | 12/1970 | Krasne | ........................ | 433/178 |
| 4,690,799 A * | 9/1987 | Yoshida | ....................... | 420/507 |
| 5,213,501 A * | 5/1993 | Watkins | ....................... | 433/172 |
| 2004/0038182 A1 * | 2/2004 | Zappini et al. | ................ | 433/178 |
| 2006/0172262 A1 * | 8/2006 | Bruce | .......................... | 433/229 |

FOREIGN PATENT DOCUMENTS

| | | |
|---|---|---|
| JP | 26-000348 B1 | 2/1951 |
| JP | 26-000350 B1 | 2/1951 |
| JP | 34-009397 B1 | 10/1959 |
| JP | 5-023358 A | 2/1993 |
| JP | 7-047089 A | 2/1995 |
| JP | 3026554 U | 7/1996 |
| JP | 2000-300584 A | 10/2000 |

* cited by examiner

*Primary Examiner* — Cris L Rodriguez
*Assistant Examiner* — Eric Rosen
(74) *Attorney, Agent, or Firm* — Birch, Stewart, Kolasch & Birch, LLP

(57) ABSTRACT

A partial denture having an artificial tooth, a denture base holding the artificial tooth, and a clasp fixed to the denture base, wherein the clasp includes a back-side arm and a front-side arm and does not include a rest, the back-side arm extending in a rearward bulging convex on a back side of a dentition-extended range of the denture base, the front-side arm extending in a forward bulging convex toward a front side of the dentition-extended range of the denture base, wherein the back-side arm and the front-side arm extend within a height range ranging from an extended plane of a top surface of a crown of the artificial tooth toward the denture base side.

17 Claims, 13 Drawing Sheets

(a)

(b)

PARTIAL DENTURE

TECHNICAL FIELD

The present invention relates to a new type partial denture provided with a clasp fitted to a root of a remaining tooth by means of two arms.

BACKGROUND ART

A partial denture is composed of an artificial tooth which substitutes for a missing tooth, a denture base to which the artificial tooth is fixed and which makes close contact with a residual ridge, a clasp which is fixed to the denture base and is removably fitted to a remaining tooth, a rest formed integrally with the clasp, and the like. The following three functions are required for the partial denture.

(A1) Supporting function against the occlusal pressure;
(A2) Retaining function against the separation force; and
(A3) Grasping function against the horizontal force applied to the denture.

The rest generally has the supporting (grasping) function, and more specifically it is considered to function as follows: (r1) to transmit the occlusal pressure applied to the partial denture to a clasped tooth (i.e., a remaining tooth that is restrained by the clasp for supporting the partial denture; also called an "anchor tooth"); (r2) to prevent sinkage of the partial denture; (r3) to hold the clasp in place; and (r4) to suppress rocking of the partial denture.

Meanwhile, the clasp is considered to prevent separation or movement of the denture base by restraining the clasped tooth with a hooked arm. More specifically, it is considered that the clasp is required to exert the following functions: (c1) to prevent separation of the partial denture by a hook portion of the arm that extends from the top of the tooth crown to the undercut of the clasped tooth to act against the separation (lifting) force; and (c2) to prevent rotation of the partial denture with an indirect retaining device as the fulcrum. With this function to prevent rotation, the clasp serves as the indirect retaining device to suppress movement of the partial denture.

The rest and clasp described above are often formed as a metal article that is cast in one piece. Alternatively, they may be formed with wire. Such a common, conventional clasp is described in Non-Patent Documents 1 and 2.

Non-Patent Document 1: "Revised New Edition, Osborne: Partial Dentures", Ishiyaku Publishers, Inc., July 1977, p. 166.
Non-Patent Document 2: Minoru Ai, "Design Manual for Partial Dentures According to Cases", Gakken Shoin, p. 36.

DISCLOSURE OF THE INVENTION

Problems to be Solved by the Invention

In a conventional clasp, as shown in FIG. 13, (a) and (b), a hooked arm 109 provided at a tip end of a fixed portion 108 fixed to an artificial tooth side extends from an upper portion of the artificial tooth side (on the left in the figure) obliquely downward away so as to surround and restrain a clasped tooth 103. It is noted that FIG. 13(a) is an elevation view of the attached state of the clasp as seen from the labial side (front side), and FIG. 13(b) is a top plan view thereof.

The hooked arm 109 is configured to surround the clasped tooth 103 from its side and from its top in three dimensions to make contact with the clasped tooth 103 in a large area, and thus, it would impose a heavy burden on the clasped tooth 103. In FIG. 13(a), the clasped tooth 103 is restrained by: a rest 110, which protrudes from a base point 111 at a tip end of a portion of a fixed portion 108 that rises from the fixed portion 108 toward a top of the tooth crown, to thereby press the top of the tooth crown of the clasped tooth from the top; and the hooked arm 109, which extends from the base point 111 obliquely downward along a protruded portion (projecting portion) of the clasped tooth to reach its undercut portion or cervical portion. Such restraint can even be compared to a three-dimensional shackle. That is, conventionally, in addition to the pressure applied from the top by the rest 110, the arm surrounding the clasped tooth obliquely from its top toward the root portion would restrain the clasped tooth 103. A heavy burden will be imposed on the clasped tooth whether the clasp is made of cast metal or wire.

In the case of providing the rest 110, it is additionally necessary to provide, by tooth cutting, a groove-shaped rest cavity for receiving the rest at the top of the clasped tooth 103. Such tooth cutting may induce cold-water pain or pulpitis. Further, if the fitting of the rest 110 into the rest cavity is incomplete, the denture base may not make sufficient contact with the residual ridge mucosa (the recovered portion after a tooth is lost), causing a gap therebetween. It is difficult to accurately check for the presence of such a gap between the residual ridge mucosa and the bottom of the denture base, and even if there is a gap, the denture deceptively appears stable and fixed, and thus it is maintained in that state. In such a case, food residues or granular matters would enter into the gap, thereby injuring the residual ridge mucosa, or even possibly causing ulcer. This would eventually increase the burden imposed on the teeth.

For manufacture of the conventional clasp, in order to ensure the three-dimensional restraint as described above, it is necessary to design the clasp by carefully calculating the shape of the undercut portion of the clasped tooth 103, which requires precision work. In particular, countermeasures against deformation due to occurrence of strain during the casting process are required. As such, the manufacture of the clasp would require advanced techniques and concentration as well as a large number of process steps.

In terms of feelings when wearing or in use, in the conventional case, the three-dimensional restraint as described above would naturally cause sense of discomfort. In addition, when chewing the food with the partial denture provided with the conventional clasp as described above, since the base point 111 of the hooked arm 109 (the connecting portion between the hooked arm 109 and the rest 110) is located at the upper end of the clasped tooth 103, the vicinity of the base point 111 serves as the fulcrum according to the principle of leverage to move the hooked arm 109, to thereby rock the clasped tooth 103. This would cause pain at the residual ridge mucosa, and the partial denture may even come off. Furthermore, since the rest directly receives the occlusal pressure, it may be broken, in which case the broken piece may be swallowed by the user. Still further, the hooked arm 109 may make contact with the tongue, lip, buccal mucosa or the like, thereby causing uncomfortable feelings, and thus, it is often the case that comfort in use cannot be obtained.

In addition, with the partial denture using the conventional clasp, a large portion of the hooked arm would be exposed on the front side, as shown in FIG. 13, (a) and (b), which cannot be covered by the denture base to be hidden from sight. As such, the hooked arm 109 remains conspicuous, which is disadvantageous in terms of aesthetics particularly for the anterior teeth portion.

As described above, the conventional partial denture have problems regarding the feelings in use or when wearing, aesthetics, difficulty level of manufacture and the like. In view of the foregoing, an object of the present invention is to provide a partial denture of a novel type that is comfortable in use and easy to manufacture.

Means for Solving the Problems

A partial denture according to the present invention includes an artificial tooth, a denture base holding the artificial tooth, and a clasp fixed to the denture base. In this partial denture, the clasp does not include a rest, and includes a back-side arm and a front-side arm, wherein the back-side arm extends in a rearward bulging convex on a back side of a dentition-extended range (imaginary; to be omitted hereinafter) of the denture base, and the front-side arm extends in a forward bulging convex toward a front side of the dentition-extended range of the denture base to make a pair with the back-side arm. The back-side arm and the front-side arm extend within a height range $S_0$ ranging from an extended plane (imaginary; to be omitted hereinafter) of a top surface of a crown of the artificial tooth toward the denture base side. The above-described height range means that the arms each have its whole length located within the range of $S_0$ shown in FIG. 7, which will be explained later as a specific example. Here, the dentition-extended range means a imaginary range extended along a real denture base.

In the configuration described above, the clasp is fitted to the clasped tooth in such a manner that the arm on the front side (labial side or buccal side) and the arm on the back side (lingual side) hold the clasped tooth at its root from a distal or mesial side of the clasped tooth. That is, the arms are put on the tooth from its respective sides, rather than squeezing it. While the clasp may easily come off from the clasped tooth with only one arm, with the two arms, the grasping force in the horizontal direction (crossing the tooth axis) increases, and thus, even if displacement occurs, it is restricted to the movement in the tooth axis direction. As such, there is almost no burden imposed on the clasped tooth, which considerably improves the sense of comfort in wearing, and it is often the case that the user even becomes unaware of the denture. Furthermore, only a small portion of the arm is exposed on the front side, which improves aesthetics. The occlusal pressure is hardly applied to the clasp; rather, it is transmitted via the artificial tooth and the denture base to the residual ridge mucosa, and thus, the clasp would very unlikely suffer damages.

In manufacture of the clasp, it is only necessary to form two arms that hold the clasped tooth at its root; the complicated and delicate shape to surround the clasped tooth from a top of the crown to the undercut portion is unnecessary. It is also unnecessary to have a rest or the like for pressing the clasped tooth from the top. Accordingly, it is possible to manufacture the clasp easily and in a short period of time. Furthermore, since the amount of the cast metal used for forming the clasp is reduced, it is possible to save precious and expensive resources. Since a rest is not provided, it is naturally unnecessary to provide the clasped tooth with a rest cavity.

As used herein, extending in a forward bulging convex means that the curved article has a curved shape which is convex toward the front side or the buccal or labial side, or in other words that the center of curvature of the curve is located on the back side (lingual side) with respect to the curved article. Further, extending in a rearward bulging convex means that the curved article has a curved shape which is convex toward the back side or the lingual side, or in other words that the center of curvature of the curve is located on the front side with respect to the curved article.

The positional relation between the artificial tooth and the front- and back-side arms can be as follows. (Directly Fitted Type): The front-side arm and the back-side arm both extend from the denture base at the root portion of the artificial tooth to extend away from the artificial tooth, wherein the back-side arm extends on the back side of the denture base in a dentition-extended direction, while the front-side arm extends from the denture base to face the back-side arm. With the partial denture of this type, both arms extend from the denture base at the root of the artificial tooth directly toward the clasped tooth that is to be adjacent to the artificial tooth.

(Fitted-At-Far-Side Type): The front-side arm and the back-side arm branch from a fixed portion, which has a back-side portion that extends from the root portion of the artificial tooth along the back side of a dentition-extended range of the denture base to go away from the artificial tooth, and a rising portion that rises in the tooth axis direction of the artificial tooth. The front- and back-side arms branch from the fixed portion and each extend in a direction approaching the artificial tooth. With this type, the fixed portion stretches out from the denture base at the root of the artificial tooth and extends along the back side of the clasped tooth that is to be adjacent to the artificial tooth, and the rising portion rises therefrom such that the clasped tooth is sandwiched between the artificial tooth and the rising portion, and then the arms extend from the rising portion in the direction approaching the artificial tooth.

More desirably, the back-side arm and the front-side arm are configured such that they extend within a height range $S_1$ whose position or location is closer to the height of an extended plane of the top surface of the denture base than to the height of the extended plane of the top surface of the crown of the artificial tooth. In this manner, it is possible to put the arms on the root of the clasped tooth more reliably, which facilitates establishment of firm fitting and comfortable sense of wearing at the same time. The above-described height range means that a most portion of each of the arms, i.e., at least three-fourth of the whole length, is located within the range of $S_1$ shown in FIG. 7, which will be described later as a specific example.

Further, desirably, the back-side arm and the front-side arm are configured such that they extend within a height range $S_2$ corresponding to a height range of a dentition-extended portion of the denture base. In this manner as well, it is possible to reliably put the arms on the root of the clasped tooth. The above-described height range means that the arms each have at least a half of the whole length overlapping the range of $S_2$ shown in FIG. 7, which will be described later as a specific example.

Furthermore, the front-side arm and the back-side arm may be configured such that they extend, in the dentition-extended portion of the denture base, within a height range $S_3$ ranging from an intermediate height position, corresponding to a height midway between a height at a top of a bottom surface of the denture base at the root of the artificial tooth adjacent to the two arms and a height at the top of the crown of the artificial tooth, toward a denture base bottom surface side. Here, that the two arms extend in the dentition-extended portion within the height range $S_3$ on the denture base side of the intermediate height position means that the arms each may have at least three-fourth of its whole length located within the height range $S_3$ that is obtained by extending the above-described height range along the dentition. More specifically, it means that at least three-fourth of the whole length of each arm extends within the range of $S_3$ shown in FIG. 7, which will be described later as a specific example. Herein, the ranges concerning the height of the partial denture of the present invention, including the above-described height range $S_3$, are called the "dentition root-portion ranges".

With this configuration, it is possible to reliably position the two arms at the root of the clasped tooth, as described above. Since the two arms are positioned at the root (cervical portion) of the clasped tooth, their movement toward the tooth axis top is hindered by contact with the side surface, such as the protruded portion, of the clasped tooth, and it is thus possible to prevent separation of the clasp or the partial denture. As a result, the retaining function (to prevent lifting or separation of the clasp) and the supporting function (to prevent tilting of the clasped tooth by fitting to the tooth root portion) are guaranteed, and a proper function as the partial denture is secured. The supporting function is attained mostly by the residual ridge mucosa, and the clasped tooth does not suffer the load for the supporting function. Further, the grasping function is sufficiently guaranteed by the residual ridge mucosa and the fitting of two or more clasps to the clasped teeth.

The partial denture described above is formed such that the front-side arm and the back-side arm of the clasp are fitted to the clasped tooth, which is a remaining tooth to which the clasp is attached, in a direction crossing the tooth axis. With this configuration, the two arms are fitted to the root portion of the clasped tooth, and thus, the occlusal pressure is not applied to the arms at the time of occlusion and the like. Accordingly, it is possible to eliminate a burden imposed on the clasped tooth via the arms, particularly the load in a direction deviated from the tooth axis direction.

Further, desirably, the back-side arm and the front-side arm each have a surface fitting to a tooth sidewall (of the clasped tooth) on a curved concave side. With this configuration, each of the arms makes face contact with the clasped tooth, which prevents tilting of the clasp, and hence of the partial denture, with respect to the clasped tooth, whereby stable fitting to the clasped tooth as well as comfortable feeling in use is ensured. As a result, the occlusal pressure or the like can be smoothly transmitted to the residual ridge mucosa. While the surface fitting to the tooth sidewall may be formed in a band shape, the width of the band does not have to be constant, which may vary at different sites.

Desirably, a maximum distance (inside measurement) Dmax across the front-side arm and the back-side arm is not less than an opening distance $D_0$ and not greater than 1.25 times the opening distance $D_0$, where the opening distance $D_0$ is a distance between a tip end of the front-side arm and a tip end of the back-side arm (inside measurement if each tip end has a certain thickness). The two distances described above are not the ones as seen in two dimensions, but the ones measured in three dimensions from the two arms of the actual partial denture.

With this configuration, it is possible to fit the clasp by putting the front- and back-side arms on the clasped tooth, without imposing a large burden on the clasped tooth. With the inventive mechanism described above where the arms are fitted to the clasped tooth in the direction crossing the tooth axis, if the above-described distance Dmax exceeds 1.25 times the opening distance $D_0$, the opening distance $D_0$ is so narrow that it will be difficult to attach the clasp to the clasped tooth, or even if it can be attached, it will be difficult to detach it. In order to facilitate attachment and detachment, Dmax is preferably not greater than 1.20 times, and more desirably not greater than 1.15 times, the opening distance $D_0$. Further, the maximum distance Dmax may advantageously be set equal to the opening distance $D_0$, in which case the burden on the clasped tooth becomes very small. The maximum distance Dmax cannot be smaller than the opening distance $D_0$ from the definition of Dmax.

Further, desirably, the front-side arm is shorter in length than the back-side arm. This ensures that the arm length exposed to the front side is reduced, which improves aesthetics.

Further, the partial denture of the present invention may include another clasp in addition to the above-described clasp. The other clasp may be configured to have a front-side arm curved in a forward bulging convex and a back-side arm curved in a rearward bulging convex, without provision of a rest. With this configuration, the other clasp can form a second fit. As a result, it is possible to form two fits with two clasps each having two arms, which ensures stable attachment of the partial denture to the clasped tooth. Such clasps for partial denture have a simple structure, impose only a small burden on the clasped tooth, and ensure comfortable feelings when wearing. They can be manufactured easily and in a short period of time, and the amount of the casting metal used is also reduced.

The above-described partial denture is formed such that the front-side arms and the back-side arms of the clasp (first clasp) and the other clasp (second clasp) are fitted to the respective clasped teeth in a direction crossing the tooth axis. With this configuration, the two clasps can stably realize the position stabilizing function i.e. the grasping function, in the direction crossing the tooth axis, while alleviating the burden on the clasped tooth and also preventing separation in the tooth axis direction. The first clasp and the second clasp can be comparative to a key and a lock of the clasped teeth.

Alternatively, the partial denture may be provided with another clasp in addition to the above-described clasp, and the other clasp may be a conventional clasp. Here, the other clasp forming the second fit corresponds to the clasp of a conventional type that has a hooked arm extending from the tooth crown side to the undercut side.

With the partial denture provided with the inventive clasp and the conventional clasp as well, comfortable feelings more than expected can be obtained when wearing. This is presumably because, when the first fit alone is provided by the inventive clasp that is fitted with two arms, the fitted portion (first fit) of the inventive clasp functions to alleviate the restraining force imposed on the clasped tooth by the conventional clasp. As a result, the user is relieved from the discomfort and strong restraining force experienced when both fits are established by the conventional clasps provided with rests.

Further, the other, second clasp may be formed at an end of a major connector that extends from the denture base on which the artificial tooth is fixed. With this configuration, for example in the case of a free-end denture, one of the two fits can be made with a remaining tooth (clasped tooth) at a distance from the artificial tooth. As a result, it is possible to enhance stability in attachment of the partial denture. The major connector may be a palatal plate, palatal bar, palatal strap or the like in the case of the upper jaw, and a lingual plate, lingual bar or the like in the case of the lower jaw.

In the case where one or more intermediate teeth are missing, it may be configured such that another clasp is not provided in addition to the inventive clasp for partial denture, and instead, the denture base is provided with a wall surface facing the clasped tooth. With this configuration, in the case where only one natural tooth is missing and there is not a sufficient space, the fit (second fit) other than the fit by the arms (first fit) can be formed by the relevant wall surface and a side surface of the natural tooth (remaining tooth) adjacent thereto. In this case, although the term "fit" for the second fit does not literally express the actual mechanism (which is in effect engagement by abutment of the surfaces), it is herein called the "fit" as an exception among the others. Even in the case where only one tooth is remaining, when this structure (abutment of the surfaces) is provided in addition to the above-described fit with two arms, the partial denture can be attached in a stable manner.

The arms of the clasp may be formed of gold-platinum alloy. With this configuration, when adjusting the arms to conform to the clasped tooth upon formation of the arms, it is possible to fit the arms to the clasped tooth with a strong fitting force, without causing breaks or the like. Further, in use, a state ensuring good and stable fitting can be maintained through repeated attachment and detachment over a long period of time. The arms made of gold-platinum alloy have a large margin for elastic deformation, which is advantageous in that attachment and detachment are easily conducted without any problems even if the arms are increased in length. Accordingly, it is possible to elongate the arms to establish firmer fitting, and thus to enhance the retaining and grasping functions.

Effects of the Invention

With the partial denture of the present invention, it is possible to provide a partial denture which relieves the clasped tooth from a large restraint, guarantees comfortable feelings when wearing, and facilitates manufacture thereof. Further, it is possible to improve aesthetics by making the front-side arm shorter in length than the back-side arm.

DESCRIPTION OF THE REFERENCE CHARACTERS

1: artificial tooth; 1*a*: top of crown; 2: fixed portion; 2*a*: back-side portion; 2*b*: rising portion; 2*d*: depression in fixed portion; 3: clasped tooth; 4: clasp arm; 4*a*: front-side arm; 4*b*: back-side arm; 5: gingival margin; 6: natural tooth next to clasped tooth; 7: base point; 8: rest; 9: hooked arm of conventional type; 10: partial denture; 11: denture base; 11*a*: top of bottom surface of denture base; 11*b*: bottom surface of denture base; 11*c*: top of upper surface of denture base; 11*w*: wall surface of denture base; 12: major connector (palatal bar); 13: height at top of bottom surface of denture base; 14: height at top of crown; 15: intermediate height between 13 and 14; 16: height at top of upper surface of denture base; 17: intermediate height between 14 and 16; 25: clasp; 103: clasped tooth to which conventional partial denture is attached; 108: conventional fixed portion; 109: conventional hooked arm; 110: rest; 111: base point of conventional clasp; F: surface abutting tooth sidewall; $S_0$, $S_1$, $S_2$, $S_3$: dentition root-portion range; $D_0$: distance at opening; $D_{max}$: maximum distance across arms.

BEST MODE FOR CARRYING OUT THE INVENTION

Hereinafter, embodiments of the present invention will be described with reference to the drawings.

First Embodiment

Figure 1:
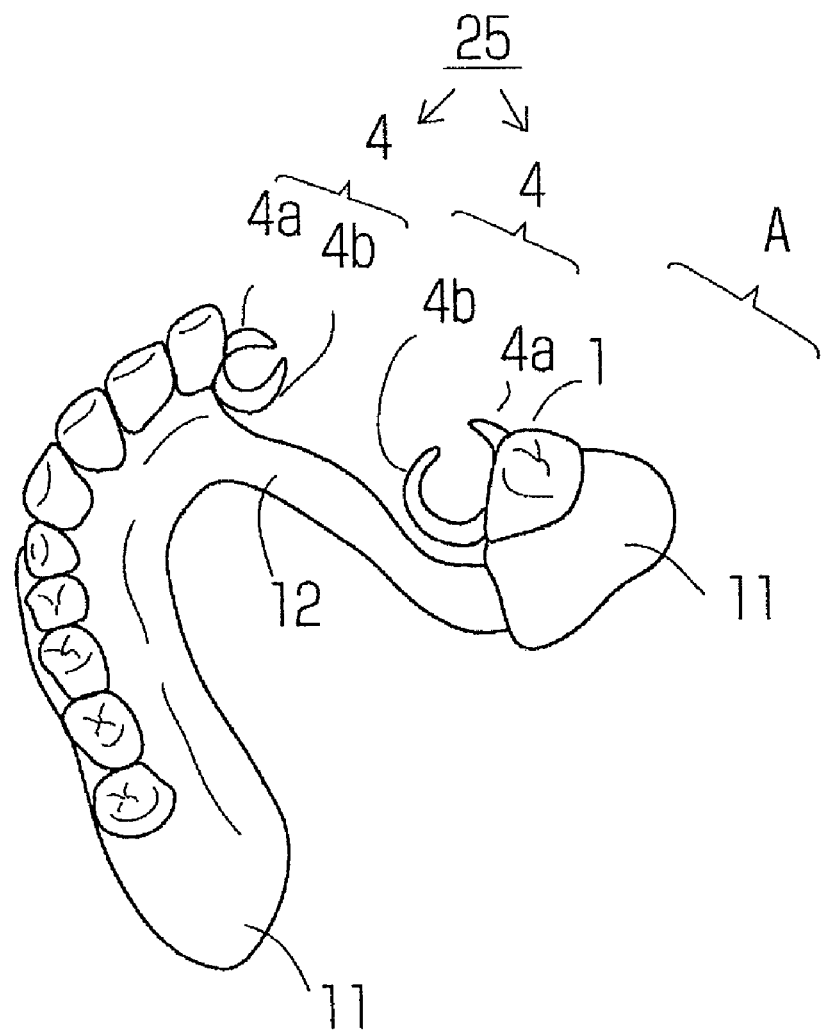
FIG. 1 It is a perspective view of a partial denture according to a first embodiment of the present invention.

FIG. 1 is a perspective view showing a partial denture 10 according to a first embodiment of the present invention. Referring to FIG. 1, the partial denture 10 of the present embodiment is for an upper jaw and provides artificial teeth for replacement of the 1st through 7th missing teeth on the right and the 1st, 2nd and 7th missing teeth on the left of the upper jaw. The remaining teeth are the 3rd through 6th teeth on the left. The artificial teeth 1 are fixed to a denture base 11 made of a resin or the like, and connected via a major connector (palatal bar) 12. The palatal bar 12 may be replaced with a plate superior to the bar in terms of supporting, grasping and retaining effects, or an arched plate making contact with an upper palate may be used together with the bar.

The partial denture 10 has two clasps 25 made of cast metal. The clasps 25 are fixed to the denture base 11, and each have a front-side arm 4*a* and a back-side arm 4*b*. The back-side arm 4*b* extends on the back side of the denture base 11 to come away from the artificial tooth 1, while being curved in a rearward bulging convex. The front-side arm 4*a* extends from the denture base to come away from the artificial tooth, opposite to the back-side arm, while being curved in a forward bulging convex. In this partial denture 10, both clasps are of a directly fitted type. In the example shown in FIG. 1, two arms 4 (i.e., mesial-side (anterior teeth-side) arm and distal-side (posterior teeth-side) arm) each have its back-side arm 4*b* longer than its front-side arm 4*a*. Further, the clasp 25 is not provided with a rest.

The two clasps are each fitted to a corresponding clasped tooth (not shown) in a direction crossing the tooth axis (i.e., horizontal direction). One clasp is fitted to the corresponding clasped tooth in the horizontal direction as a key, while the other clasp is fitted to the corresponding clasped tooth in the horizontal direction as a lock. The clasp serving as the key and the clasp serving as the lock are generally fitted in the order of key and then lock, although there are cases where the order does not matter. When removing the partial denture, the lock and then the key are disengaged, although there are cases where the order of disengagement does not matter upon removal as well. With the two fits provided by the key and the lock, it is possible to improve the grasping function particularly against the horizontal force imposed on the partial denture.

Figure 2:
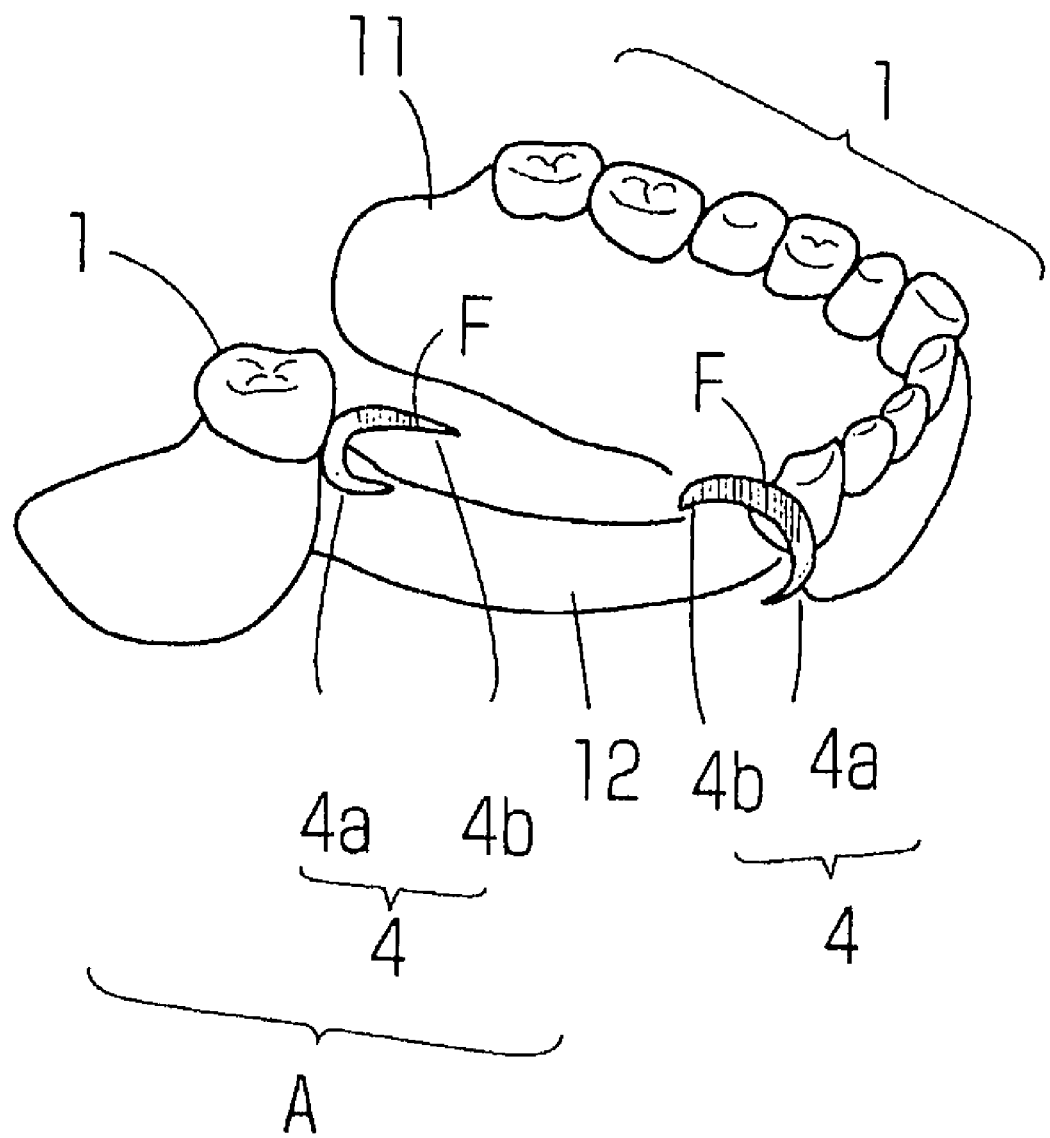
FIG. 2 It is a perspective view of the partial denture in FIG. 1 as seen from another direction.
Figure 3:
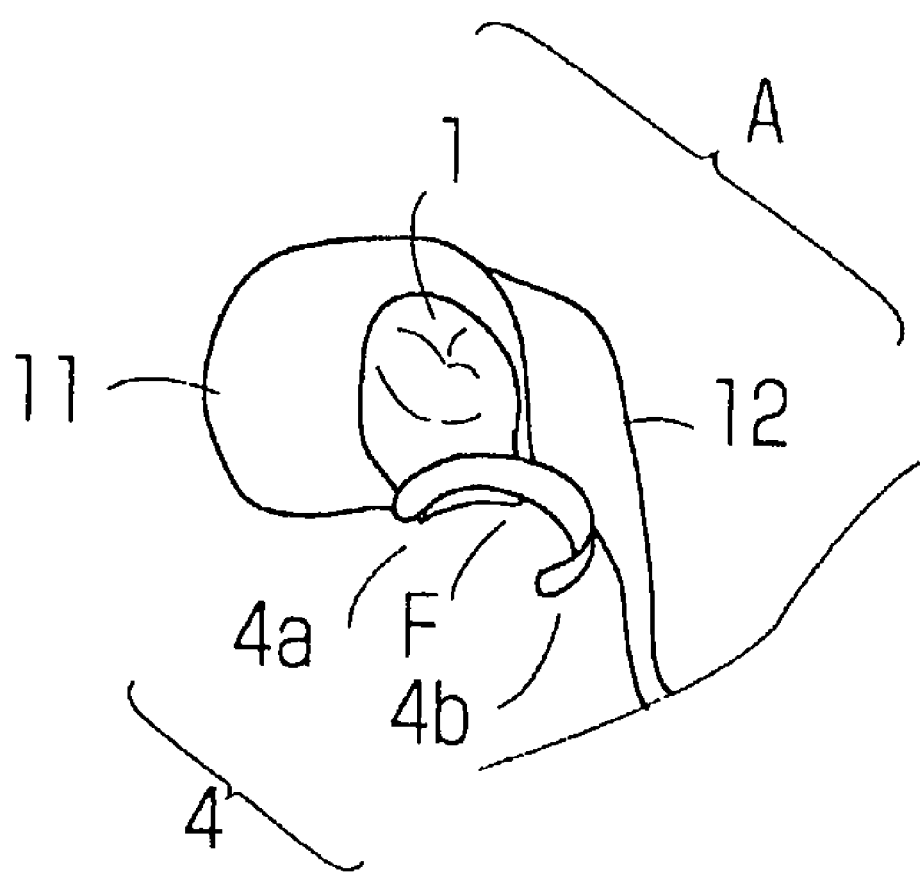
FIG. 3 It is a perspective view of an A portion of the partial denture in FIG. 1.

FIG. 2 is a perspective view of the partial denture 10 shown in FIG. 1, with the arms seen from another direction. Each of the two arms 4 has a concave surface side (making contact with the clasped tooth) on which a band-shaped surface F abutting a tooth sidewall is formed to achieve face contact with the clasped tooth. The two arms 4 each extend, in a dentition-extended portion of the denture base 11, within a height range in a denture base 11 side limited by a top of a crown of the artificial tooth 1. FIG. 3 is a perspective view of only the A portion shown in FIGS. 1 and 2. The arm 4 is arranged adjacent to the 7th tooth on the left which is an artificial tooth, and the back-side arm 4b and the front-side arm 4a extend from the denture base to hold the 6th tooth on the left serving as a clasped tooth.

With the above-described structure, the long back-side arm 4b and the shorter front-side arm 4a are put on the root of the clasped tooth and are fitted to the clasped tooth in such a manner to embrace or hold the clasped tooth in the arms. Thus, the burden imposed on the clasped tooth is very small, which even makes the user unaware of the denture. This is because the retaining and supporting functions are achieved by the residual ridge mucosa with which the denture base 11 comes into close contact. Further, in the case of the partial denture shown in FIG. 1, the grasping function is obtained by the two clasps 25 differing in opening direction from each other.

The front-side arm 4a is short, which avoids impairment of aesthetics. Further, with each clasp 25 of the partial denture 10, it is unnecessary to arrange the arms around the clasped tooth while changing the height position from the crown top portion to the undercut portion of the clasped tooth. This ensures a simple structure and easy manufacture. As such, a partial denture giving an excellent wearing or use feeling can be provided in a short period of time, without the need of advanced techniques.

Figure 4:
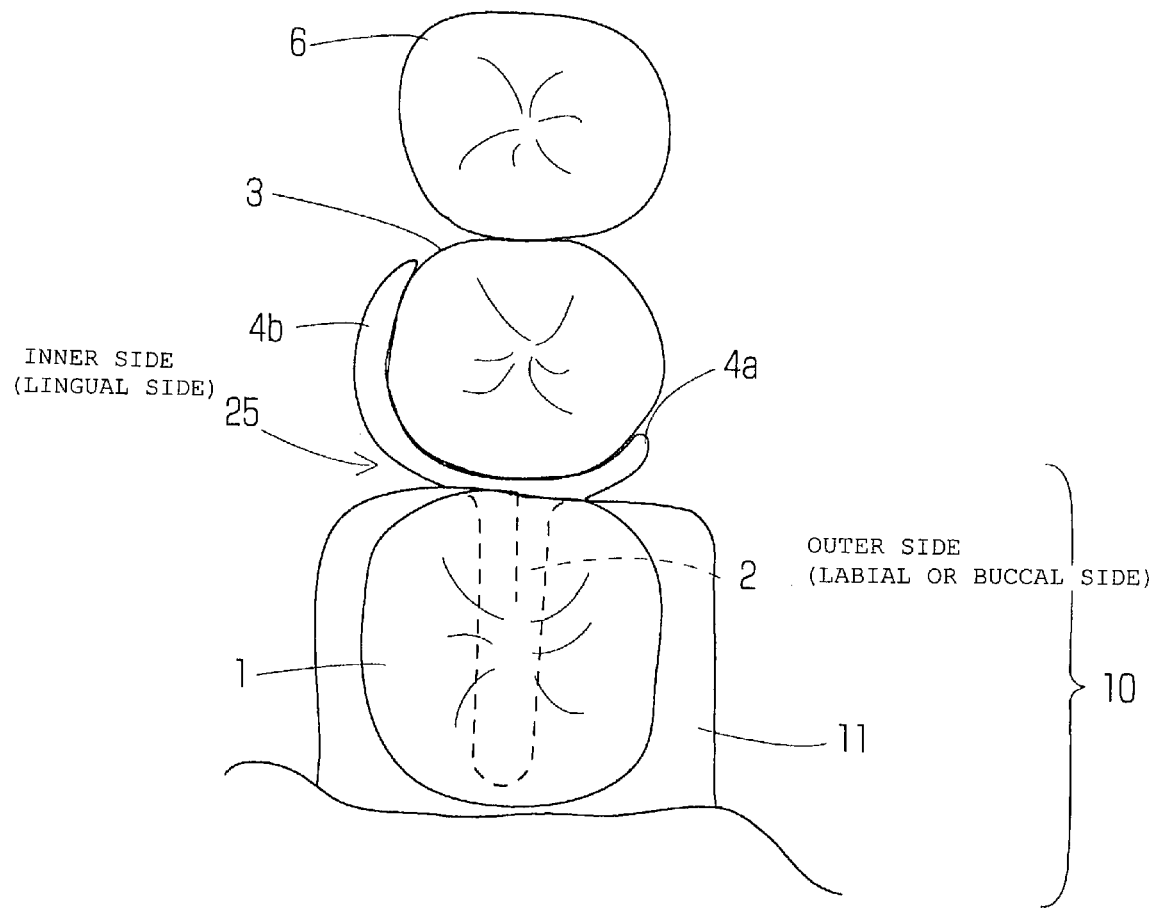
FIG. 4 It is a plan view of the partial denture in FIG. 1 when it is attached to a clasped tooth, as seen from the crown top side to the denture base side.

FIG. 4 is a top plan view of the partial denture 10 in an attached state, as seen in the direction from the tooth tip toward the tooth root of the artificial tooth. The major connector is not shown in the figure. The clasp is provided with a fixed portion 2, and a back-side arm 4b and a front-side arm 4a of a forked shape branched from the fixed portion 2. The fixed portion 2 is embedded in the denture base (made of a resin) 11 beneath the artificial tooth (on the side farther from the tooth crown). Although the fixed portion 2 of a bar shape is shown in the figure, it may be formed into a mesh or lattice form integrally with the two arms, in order to increase the contact area with the resin of the denture base 11.

Branched from the fixed portion 2, the front-side arm 4a is generally shorter than the back-side arm 4b. If the back-side arm is too long, however, it may exceed a half of the circumference of the clasped tooth. In a conventional clasp, the front- and back-side arms are both configured to extend as long as possible to maximize the three-dimensional restraining force as described above, and thus, they are often equal in length.

Figure 5:
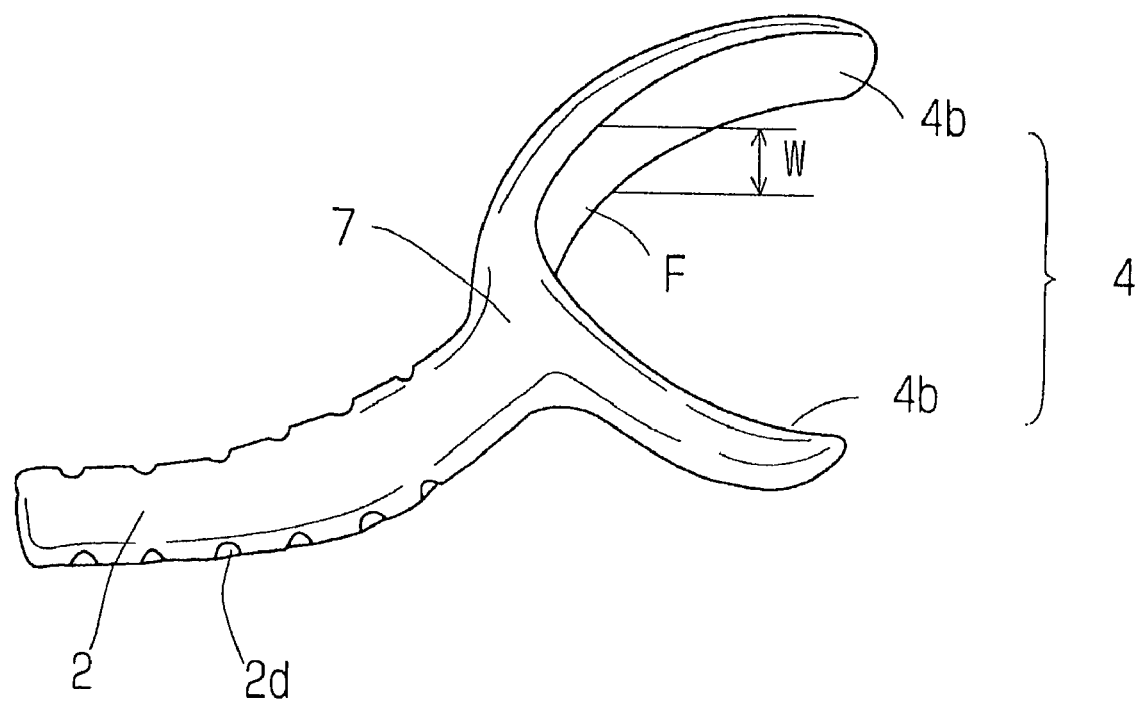
FIG. 5 It is a perspective view showing a forked clasp.

FIG. 5 is a perspective view of a clasp made of cast metal, shown in a state separated from a denture base. It is desirable that the two arms 4a and 4b each have a band-shaped surface having a width W in order to guarantee sufficient contact with the side surface of the clasped tooth. The specific value for the width W will be explained later. The fixed portion 2 is desirably provided with a depression 2d to guarantee contact with the denture base. It may be formed in a mesh or lattice form, as described above. The clasp 25 is formed of gold, platinum, gold-silver-palladium alloy, titanium, cobalt chrome, nickel chrome, or other metal, alloy or the like. It may be formed integrally using a plastic (resin) as a raw material. Namely, the clasp 25 may be formed of a same plastic as the plastic (resin is a kind of plastic) forming the denture base, extending from the denture base. It has been confirmed that a clasp formed of a resin or the like will suffer no problem in the meantime. When the clasp arms are made of gold-platinum alloy, in the case of adapting the arms to the clasped tooth upon formation thereof, it is possible to fit the arms to the clasped tooth with a stronger fitting force, compared to the ones made of cobalt chrome for example, without causing breaks or the like. Further, it is possible to maintain a shape ensuring a good and stable fit for a long period of time through repeated attachment and detachment while in use. The arm made of gold-platinum alloy has a large margin for elastic deformation, which is advantageous in that attachment and detachment are easily conducted even if the arms are increased in length. Accordingly, it is possible to elongate both arms to guarantee a firmer fit, to thereby further increase the retaining and grasping functions without causing any problems in attachment to and detachment from the clasped tooth in a direction crossing the tooth axis.

The above-described clasp 25 for partial denture may be manufactured by casting, bending or the like to have a shape conforming to the clasped tooth (remaining tooth) 3 or the status of the residual ridge of the missing tooth in advance. Alternatively, it may be manufactured by forming one in a prescribed shape as a ready-made article and by applying deformation thereto as appropriate.

Figure 6:
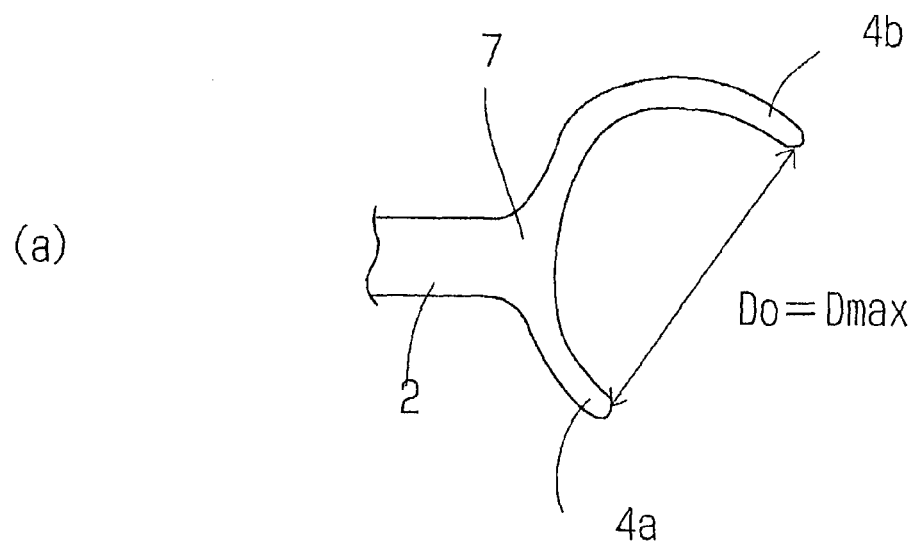
FIG. 6 It is a diagram showing arms of the clasp, wherein (a) shows the case where a distance at the opening and a maximum distance across the arms are equal, and (b) shows the case where the maximum distance is greater than the opening distance.
Figure 6:
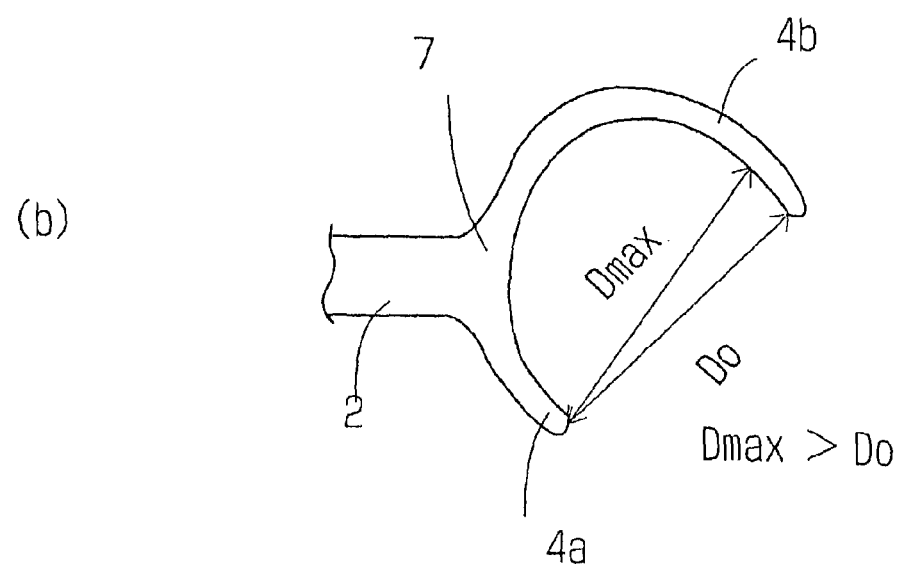

FIG. 6 is a plan view of the clasp, where FIG. 6(a) shows the case where a distance $D_0$ at an opening between the tip ends of two arms 4a, 4b is equal to a maximum distance Dmax across the arms, and FIG. 6(b) shows the case where the opening distance $D_0$ between the tip ends of two arms 4a, 4b is smaller than the maximum distance Dmax across them. The present invention is applicable to both the cases shown in FIG. 6(a) and FIG. 6(b). Although it may be seen in FIG. 6, (a) and (b), that the opening distance $D_0$ and the maximum distance Dmax are measured in two dimensions, they are actually measured for a real thing (in three dimensions).

In the case of FIG. 6(a), the distance across the arms remain approximately the same as the opening distance $D_0$ in the vicinity of the opening end, while the arms extend toward the arm root side for a certain distance. Alternatively, it may be configured such that the distance across the arms decreases monotonously from the opening end toward the arm root side. This is because the two clasps, different in opening direction from each other, can prevent separation in the lateral direction. As to separation in the tooth axis direction, since the two arms are put on the root of the corresponding clasped tooth as described above, the contact between the protruded portion of the clasped tooth and the arms can prevent such separation.

In the case of a conventional clasp, the maximum distance Dmax across the two arms, measured as described above, is 1.3 times at the smallest and normally at least 1.5 times the opening distance $D_0$. This is because conventionally the opening distance is reduced to the smallest possible extent allowing attachment, for the purpose of enhancing the restraining force.

It is also possible to form the front-side arm and the back-side arm as a forked arm that branches from a single fixed portion embedded in the denture base, as shown in FIG. 5 explained above. With this configuration, the clasp can be formed by forming a structure of one fixed portion and frontand back-side arms branching therefrom as one piece by metal casting, and by embedding the same in the denture base. As a result, it is possible to manufacture a partial denture including the clasp easily and in a short period of time.

When in use, it is possible to attach the clasp by putting the front-side arm 4a and the back-side arm 4b on the clasped tooth to sandwich it between the arms. This facilitates attachment of the clasp to the clasped tooth, and the two arms 4a, 4b are fitted around the clasped tooth with a sufficient fitting force, thereby preventing deviation of the partial denture in a lateral direction.

Accordingly, the undesirable event of the occlusal pressure being applied obliquely to the clasped tooth is avoided, and the occlusal pressure is smoothly transmitted from the artificial tooth to the residual ridge mucosa, and the arms maintain the state fitted to the side portion of the clasped tooth. As a result, comfortable feelings in use are ensured at the time of occlusion or other time, without imposing a burden on the clasped tooth. Furthermore, in the case where only one tooth is remaining and it is even rocking, such movement of the tooth will rather be alleviated, as long as the above-described state is maintained and cleanliness is kept.

The fixed portion 2 is about 7 mm in length and about 2 mm in width W, and is embedded in the denture base for fixation. The arms 4a, 4b may be tapered, or the tip ends may have the same width as the other portions. It is preferable that the arms 4a, 4b have the width W of about 2 mm except for the tip ends.

Figure 7:
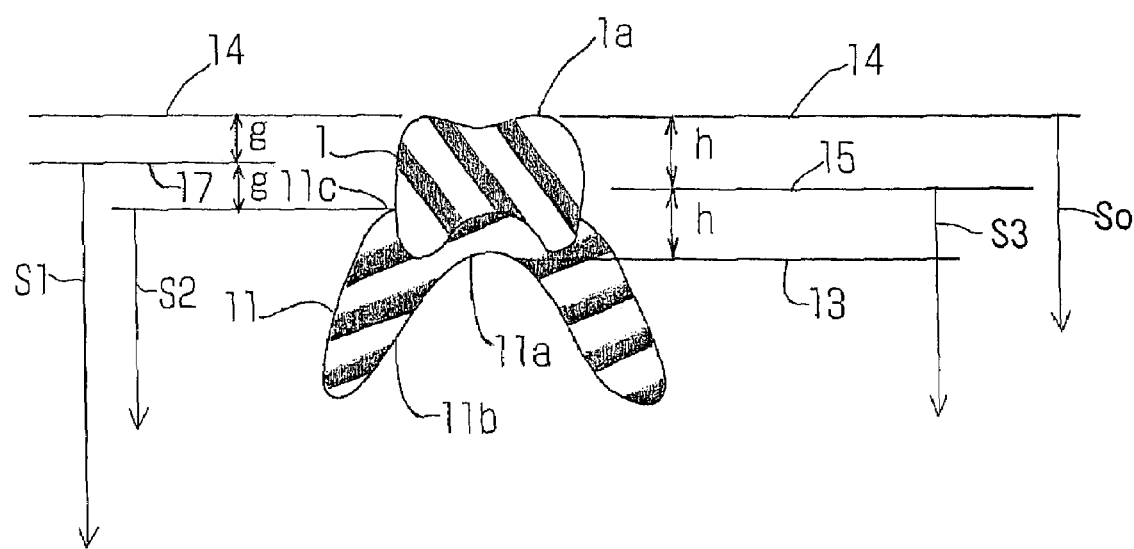
FIG. 7 It is a cross sectional view through an artificial tooth in the partial denture of the present invention.

FIG. 7 is a cross sectional view of a portion of the artificial tooth adjacent to the clasp. The front-side arm and the back-side arm (both not shown) have their whole lengths located within a height range $S_0$ located in a denture base side limited by a height of a top 1a of the tooth crown. Alternatively, each of the two arms may be arranged within a height range where at least a half of its whole length overlaps a height range $S_2$ in the denture base root side limited by a top 11c of an upper surface of the denture base 11. This ensures that the arms are fitted to the root of the clasped tooth.

More preferably, the arms are located within a height range closer to a height of an extended plane of a top 11c of the denture base than a height of an extended plane of the top 1a of the crown of the artificial tooth. This height range corresponds to a height range $S_1$ ranging from an intermediate height 17 between the height 14 at the top 1a of the crown of the artificial tooth and the height at the top 11c of the upper surface of the denture base toward the denture base root side. Although it is desirable that the arms have their whole portions located within the height range $S_1$, it is sufficient that at least three-forth of their lengths is located within the height range $S_1$.

It is further preferable that the arms each have at least three-fourth thereof located within a height range $S_3$ in FIG. 7. The intermediate height position 15 is located midway between a height 13 at a top 11a of a bottom surface 11b of the denture base 11 and the height 14 at the top 1a of the crown of the artificial tooth 1 located at an end of the partial denture. The front-side arm 4a and the back-side arm 4b are each located, in the dentition-extended portion, within the height range $S_3$ in the denture base bottom surface 11 side limited by the intermediate position 15. As described above, the height ranges $S_0$, $S_1$, $S_2$, and $S_3$ refer to the dentition root-portion ranges.

Although it is not clearly understood that FIG. 7 is about the dentition-extended portion, it can be considered that there will be no difference between the height range at the cross sectional site of the artificial tooth adjacent to the arms and the height position at the site where the relevant height range is imaginarily extended from the dentition to the position of the arms. The same applies to the dentition root-portion ranges $S_0$, $S_1$, and $S_2$ described above as well. As to each of the height positions of the top 1a of the crown and the top 11c of the upper surface of the denture base, if there is a difference between the front side and the back side, an average thereof is taken.

As described above, when both arms have their whole lengths located within the dentition root-portion range $S_0$ and have at least a half thereof located within the height range $S_2$, it is possible to position the arms along the cervical portion (root of the exposed portion) of the clasped tooth 3. More desirably, when at least three-forth of the whole length of each arm is located within the dentition root-portion ranges $S_1$, $S_3$, it is possible to more reliably position the arms 4a, 4b along the cervical portion (root of the exposed portion) of the clasped tooth 3.

The fixed portion 2 and the arms 4a, 4b are arranged in an approximately flat plane, unlike the three-dimensional structure of a conventional clasp that extends circumferentially from a top of the tooth crown to the undercut (on the root side lower than the protruded portion). In other words, while the conventional clasp is curved to surround the circumference of the clasped tooth as seen in two dimensions and is also curved to be concave toward the tooth crown top side and convex toward the root side as seen from both of the buccal side and the lingual side, the above-described clasp is curved only in two dimensions, and is hardly curved as seen from the buccal side and the lingual side.

Figure 8:
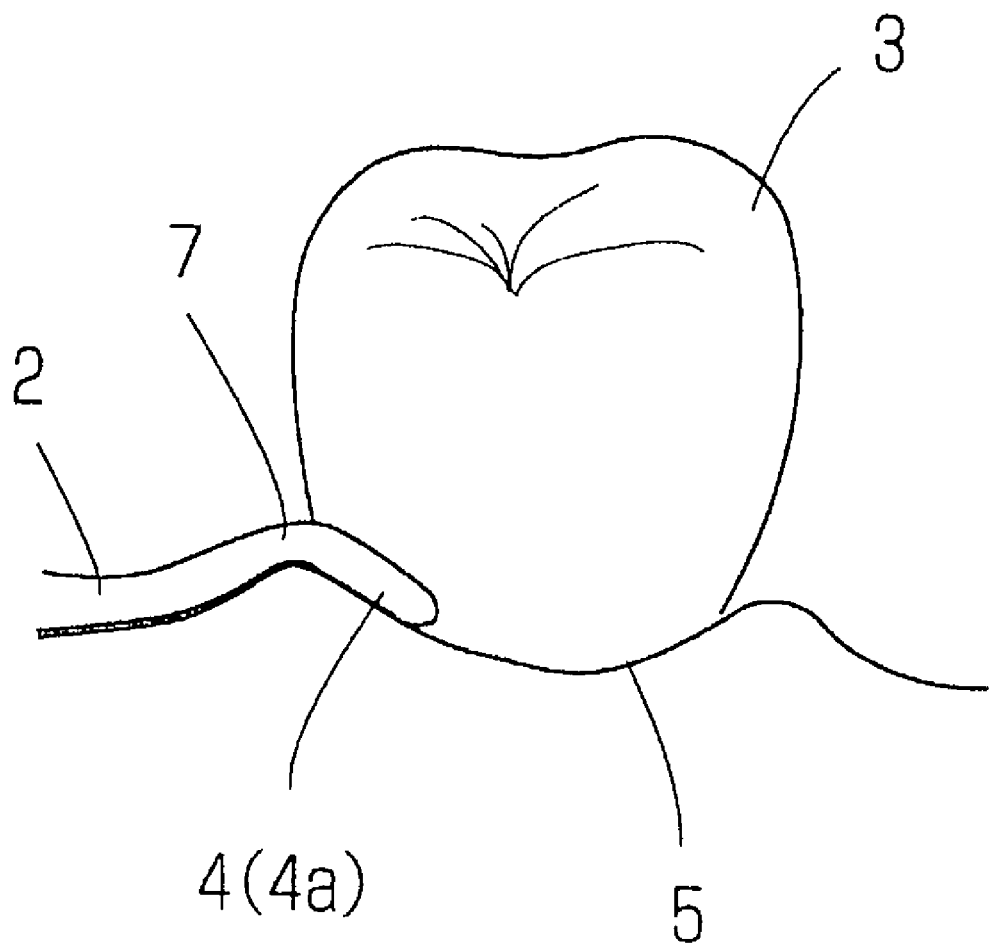
FIG. 8 It is a perspective view showing a front side of the clasped tooth when the partial denture of the present invention is attached thereto.

Generally, the two arms 4a, 4b have an approximately C shape in three dimensions. The vicinity of the connecting portion between the arms 4a, 4b and the fixed portion 2 makes contact with the clasped tooth 3 at an upper portion of the gingival margin 5 on the mesial or distal side of the clasped tooth 3 (it is desirable that it is as close to the gingival margin 5 as possible, or it may be in contact with the gingival margin 5). With the center of the vicinity of the connecting portion as a base point 7, the portion 4a (see FIG. 8) extends to the front side of the clasped tooth, or the front side (labial or buccal side), along the gingival margin 5, while the portion 4b extends to the back side of the clasped tooth, or the back side (lingual side). The two arms 4a, 4b are advantageously placed as close to the gingival margin 5 as possible.

When the major portions of the arms 4a, 4b have the width W of not less than 1 mm, they can make face contact with the side portion of the clasped tooth 3, ensuring a more stable attached state. The width W of each of the arms 4a, 4b may be changed as appropriate in accordance with the size of the clasped tooth 3, in a range of about 1 mm to about 3 mm. The arms 4a, 4b may have an approximately semicircular cross section with a thicker central portion, although they may be in the form of a plate having a relatively small thickness.

In the case where the contact state of the arms 4a, 4b with the clasped tooth 3 is not so close, a window (hole) is provided in the contact surface of the arm. Although the window is advantageously provided in the contact surface with the clasped tooth 3 in the vicinity of the base point 7, it may be provided at a position away from the vicinity of the base point 7. When a resin or other plastic material is provided into the window and cured within the oral cavity, an appropriate friction force is achieved while a retaining force not imposing a burden on the clasped tooth 3 is obtained. Although the window in the contact surface may be provided upon manufacture of the clasp, it may be cut and provided while testing how they fit.

It is desirable that the arms 4a, 4b would not surround the clasped tooth 3 longer than needed; otherwise, it would become difficult to remove the arms from the clasped tooth 3.

It is also desirable, as described above, that the front-side arm 4a is exposed as little as possible in terms of aesthetics.

In this regard, the portion 4a of the clasp arm 4 extending on the labial or buccal side only needs to have a length sufficient to be located within a range of one-fourth to one-third of the mesial side of the clasped tooth 3, much closer to the artificial tooth 1 with respect to the center of the clasped tooth 3 on the labial or buccal side. By comparison, the portion 4b of the clasp arm 4 extending on the lingual side is configured to extend to the opposite side of the base point 7 (i.e., to the distal side if the base point 7 is on the mesial side, or to the mesial side if the base point 7 is on the distal side), which can further enhance the retaining function.

More specifically, the portion 4a of the clasp arm 4 extending on the labial or buccal side only needs to extend to surround the clasped tooth 3 a little (about 1 mm to about 2 mm), while the portion 4b of the clasp arm 4 extending on the lingual side needs to surround about 70% to about 90% in width of the lingual surface of the clasped tooth 3. The clasp arm 4 as a whole makes contact with the vicinity of the gingival margin 5 of the clasped tooth 3 in an approximately horizontal state, and may have a length sufficient to surround about a half, or less, of the entire circumference thereof. This means that the clasp arm can be made considerably shorter than that of the conventional clasp for partial denture.

With this clasp arm 4, the portion 4b extending on the lingual side, which is put softly onto the clasped tooth 3, mainly supports the clasped tooth 3, while the portion 4a extending on the labial or buccal side is slightly hooked onto the clasped tooth 3. This configuration works well to restrict the moving direction (attaching and detaching direction) of the denture to the longitudinal direction (vertical direction) of the clasped tooth 3.

That is, with this clasp for partial denture, the clasp arm 4 makes contact with the clasped tooth 3 on the labial or buccal side and on the lingual side at a portion close to the gingival margin 5, so that it is slidable only in the longitudinal direction of the clasped tooth 3. As such, the partial denture moves only when a force is applied to the longitudinal direction of the clasped tooth 3. At the time of normal occlusion, no force is applied to the longitudinal direction of the clasped tooth 3, and thus, the denture would not move or come off unless the force is intentionally applied to the longitudinal direction of the clasped tooth 3. Close contact with the mucosa is ensured and sufficient masticatory ability is guaranteed, and accordingly, the user can masticate without anxiety and also can yawn and sneeze freely. The denture can be attached and detached very easily by applying a force in the direction crossing the tooth axis, and the user can readily master how to attach and detach the denture.

Further, compared to a conventional clasp where the clasp arm 4 is adapted to surround the clasped tooth 3 over the almost entire circumference, this clasp for partial denture is shorter in length and makes a much lighter contact with the clasped tooth 3, so that it exerts no function on the clasped tooth 3 when the denture is stationary. Moreover, the burden imposed on the mucosa and the periodontal ligament is very small. As such, even in the state where the user puts on the denture, he/she feels it very light in weight and even feels as if they were his/her own teeth. Even when the denture moves upon occlusion, the burden on the clasped tooth 3 is small, and the force applied to the clasped tooth 3 can escape at the portion not provided with the clasp arm 4. In addition, the shorter length results in a smaller amount of raw materials required. Since the amount of metal used is small, the clasp can be manufactured at a low cost, particularly in the case of using expensive metal such as gold alloy or gold-platinum alloy.

Further, with this clasp for partial denture, the clasp arm 4 makes contact with the region near the gingival margin 5, i.e., approximately at the center of the clasped tooth 3 in the vertical direction of the tooth, and is considered to exert maximum working force and maximum repulsive force with respect to the center in the vertical direction of the tooth, whether it is a normal tooth or a rocking tooth. Accordingly, a firmly fitted state is guaranteed despite a soft contact with the clasped tooth 3, and the clasp applies almost no force to the tooth in the lateral direction (crossing the toot axis direction) while supporting the tooth. As such, the clasped tooth 3 may be either a vital tooth or a non-vital tooth, and the clasped tooth 3 may even be a tooth that rocks to a certain degree. Rather, putting on the denture using this clasp may prevent movement of the rocking tooth and eliminate the pain at the time of occlusion. Unlike the denture using a conventional clasp, it is often the case that the user does not need to remove the denture, and even prefers keeping the denture putted on, instead of removing it. In the case where the rocking tooth causes pain at the time of occlusion and the like, the contact with the clasp would rather reduce such pain.

The clasp is applicable regardless of the size of the missing portion. Even if only one tooth is remaining, the tooth can be used as the clasped tooth 3. Further, while the clasp is applicable regardless of the number of missing teeth, it is effective particularly when used for a single denture, compared to a conventional clasp. That is, if conventional clasps are used for a single denture, a pair of clasps are hooked onto the clasped teeth at the respective sides of the missing portion for fixation, in which case despite the advantage that one tooth is provided in the missing portion by the single denture, the considerable burden imposed on each of the neighboring clasped teeth causes the user to feel very uncomfortable, although at present the user endures such discomfort. Such a problem can be solved by using the inventive clasp.

In terms of aesthetics as well, with this clasp for partial denture, the portion 4a of the clasp arm 4 extending on the labial or buccal side is located near or makes contact with the gingival margin 5, and the portion 4a can be very short in length, which can easily be hidden from sight by covering the same with a resin. For example, when a white resin adhesive to a resin of the denture base is bonded to an extension of the resin of the denture base, it is possible to hide the metal color of the clasp arm 4. When a resin of the same color as the tooth is used, it becomes completely inconspicuous. Further, when this clasp for partial denture is covered with a resin, the clasp and the denture become one piece, which eliminates the problems of the conventional clasp such as entering of the food residues and the like, and also ensures that a cleaner state can be kept.

Further, the clasp arm 4 is relatively thick in width and short in length, and makes contact with the denture base. As such, it would unlikely be broken or damaged, which prevents the undesirable situations as in the conventional clasp that it damages the buccal mucosa, tongue and others in the oral cavity of the user, and that the user swallows the broken piece. Furthermore, it will hardly suffer deformation during a long-term use.

It is unnecessary to provide the clasp with a rest for fixation of the denture, or perform tooth cutting to form a rest cavity in the clasped tooth 3. Accordingly, it is possible to eliminate the undesirable event of occurrence of a gap due to incomplete contact between the denture base and the mucosa, as well as induction of cold-water pain or pulpitis due to tooth cutting, which would have occurred when applying the conventional clasp provided with a rest.

Moreover, it is unnecessary to design the clasp taking into consideration the shape of the undercut portion of the clasped tooth 3, as in the case of designing a conventional clasp. The manufacture is very easy, because precision work is unnecessary and the clasp is short in length and simple in shape as a whole. Furthermore, with this clasp, it is often the case that there occurs no difference in the fixed state of the denture whether the clasp arm 4 is applied to the clasped tooth 3 from the mesial side or the distal side.

Second Embodiment

Figure 9:
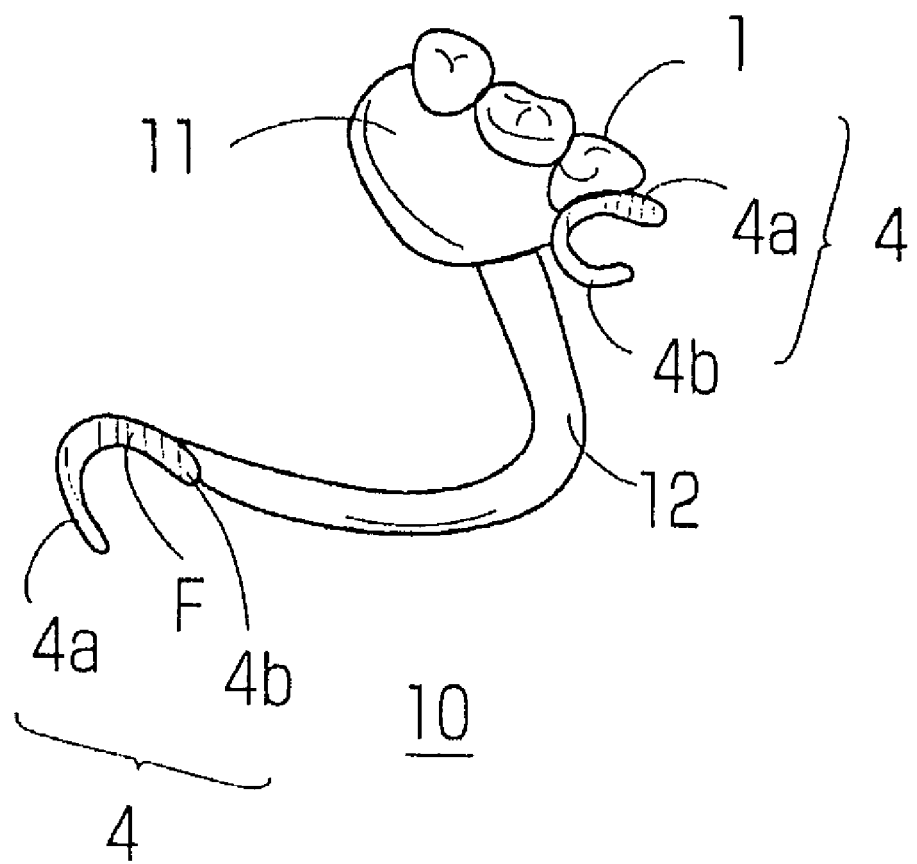
FIG. 9 It is a perspective view of a partial denture according to a second embodiment of the present invention.

FIG. 9 is a perspective view showing a partial denture 10 according to a second embodiment of the present invention. The partial denture 10 of the present embodiment substitutes for the 5th through 7th missing teeth on the right side of the upper jaw. The two arms 4, each formed of a back-side arm 4b and a front-side arm 4a, are connected via a palatal bar 12 serving as a major connector. This partial denture 10 has clasps of a directly fitted type.

Regarding the height range of the two arms, each arm is located such that its whole length is within the range of $S_0$, that at least a half of the whole length overlaps the height range $S_2$ of the denture base 11, and that at least three-fourth of the whole length is within the height ranges $S_1$ and $S_3$. This ensures that each arm is reliably fitted to the root of the clasped tooth, while hardly imposing a burden on the clasped tooth. Accordingly, it is possible to provide a partial denture giving a comfortable feeling when wearing.

Third Embodiment

Figure 10:
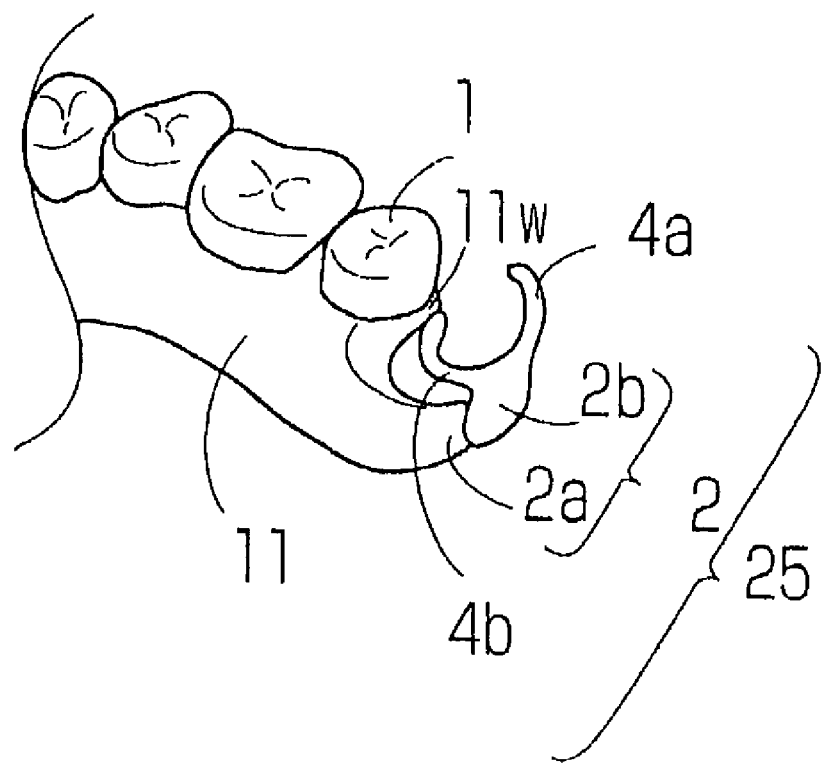
FIG. 10 It is a perspective view of a partial denture according to a third embodiment of the present invention.

FIG. 10 is a perspective view showing a partial denture according to a third embodiment of the present invention. The present embodiment shows an example where a partial denture is fitted using only one remaining tooth (7th tooth on the upper jaw) as the clasped tooth. In FIG. 10, the clasp 25 includes: a back-side portion 2a that extends from the artificial tooth 1 located at an end to go around the back side of the clasped tooth (not shown); a rising portion 2b that rises from the back-side portion 2a along the tooth axis; and arms 4a, 4b that branch and extend in two ways from the rising portion 2b. The back-side portion 2a and the rising portion 2b constitute a fixed portion 2. This partial denture 10 has a clasp of a fitted-at-far-side type.

In the present embodiment, the arms 4a, 4b implement a single fit to the unshown clasped tooth. Although a partial denture usually requires two fits, the other fit is implemented by abutment of a wall surface 11w at an end of the denture base with a side surface of the unshown clasped tooth. Naturally, the abutment would not exert such a large restraining force on the clasped tooth as in the case of the fitting by a conventional hooked arm. The clasped tooth is sandwiched between the wall surface 11w at the end of the denture base and the arms 4a, 4b, so that it is possible to implement secure attachment without imposing a large load on the clasped tooth. As a result, even if the single clasped tooth is a rocking tooth, when it is sandwiched between the wall surface 11w at the end of the denture base and the arms 4a, 4b, the rocking tooth is stabilized and firmly secured at the time of attachment of the denture and at the time of occlusion, and its movement is rather suppressed.

Figure 11:
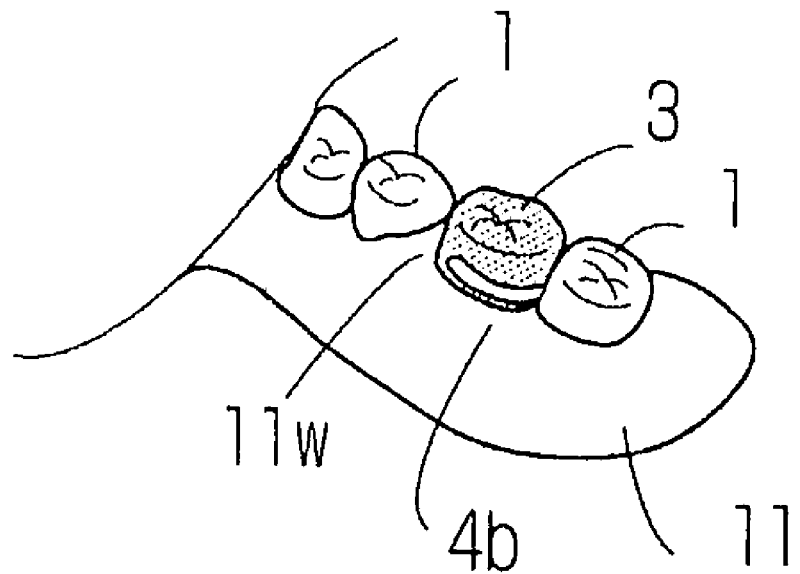
FIG. 11 It is a perspective view showing a modification of the partial denture according to the third embodiment of the present invention.

FIG. 11 shows a modification of the partial denture according to the third embodiment described above. In FIG. 11, the arm 4b is considerably increased in width. With such a widened arm, the contact area between the arm 4b and the side surface of the clasped tooth 3 increases, which is effective in stably holding the posture of the clasped tooth when it is a rocking tooth. In this case, it is important that at the opposite side from the arm-contact side of the clasped tooth, the wall surface 11w of the denture base comes into contact with the side surface of the clasped tooth 3 for supporting the same. In FIG. 11, the wall surface 11w provided at the denture base and facing the clasped tooth 3 is shown slightly wider with exaggeration, for ease of understanding.

Such a widened arm may be used not only in the case where only one tooth is remaining and the other 13 teeth are missing, but also for example in the case where a tooth having a small undercut is to be used as the clasped tooth, so as to cover the major portion of the sidewall of the clasped tooth. In this case, although the arm may exceed a half the height of the tooth crown portion, such widening will not pose any particular problem.

Fourth Embodiment

Figure 12:
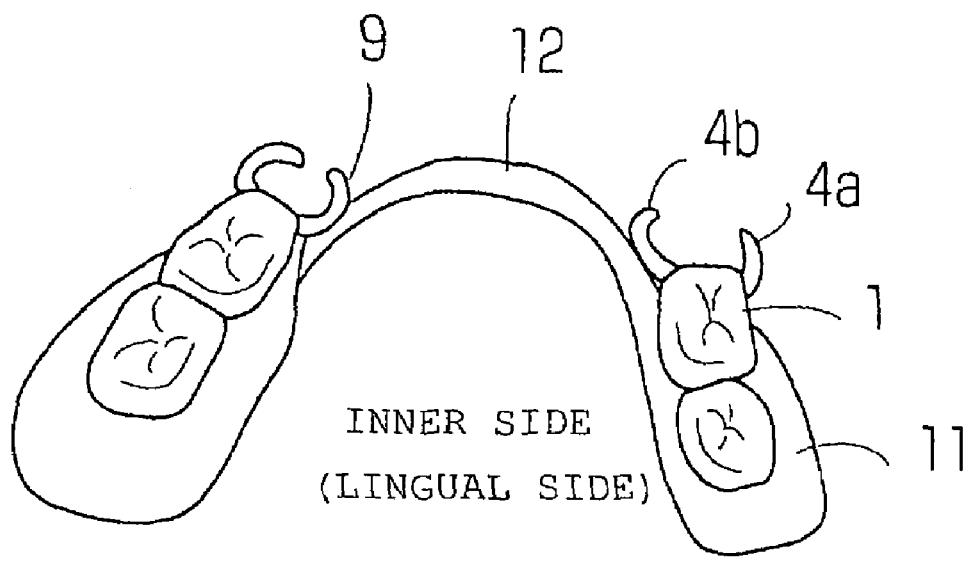
FIG. 12 It is a perspective view showing a partial denture according to a fourth embodiment of the present invention.
Figure 13:
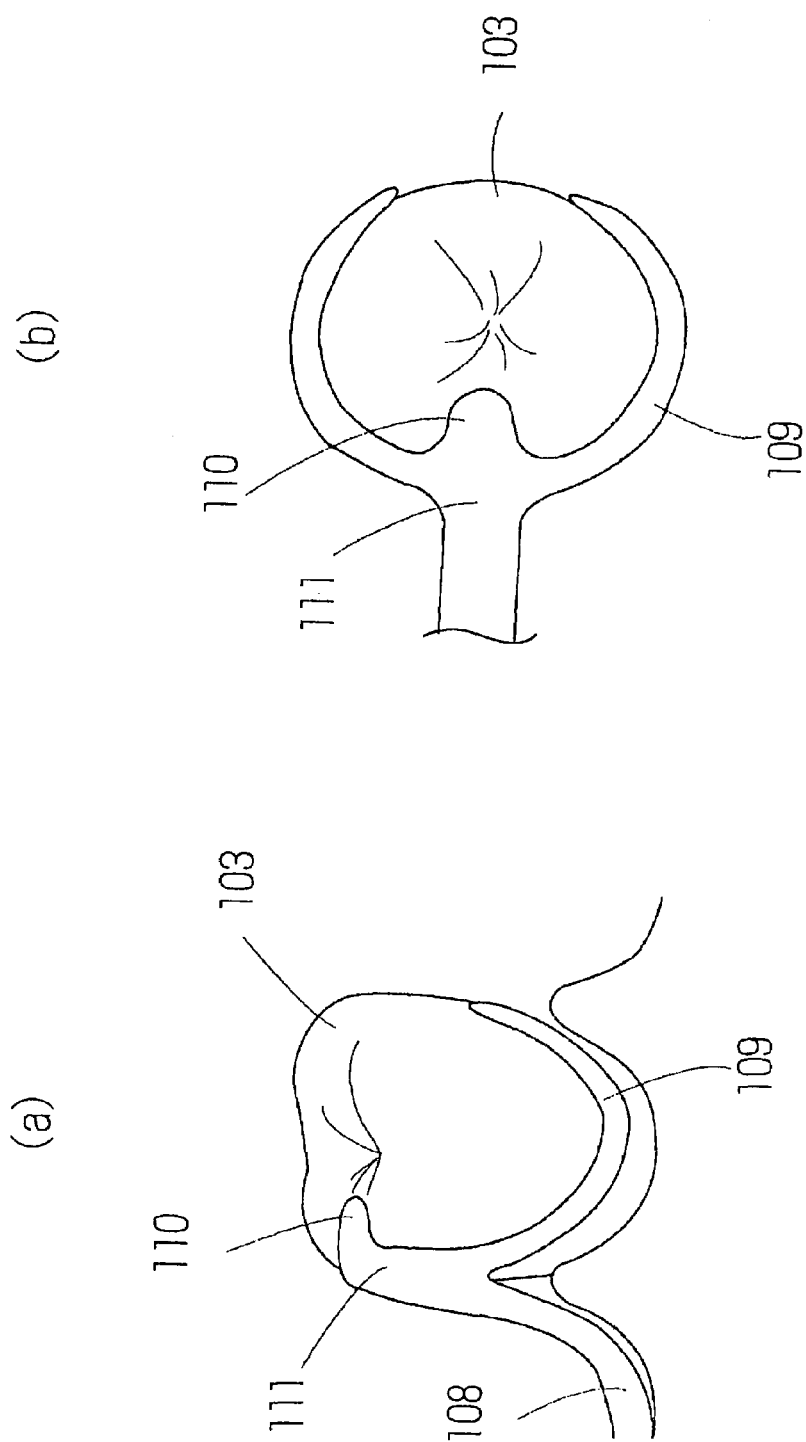
FIG. 13 It is a diagram showing the state where a conventional partial denture is attached, wherein (a) is a front view as seen from the buccal side, and (b) is a top plan view thereof.

FIG. 12 is a perspective view showing a partial denture according to a fourth embodiment of the present invention. The present embodiment introduces an inventive partial denture having one clasp formed with two arms as explained above and the other clasp of a conventional type. In this partial denture of the present invention, as shown in FIG. 12, it is possible to use the inventive clasp together with the clasp having a conventional arm 9. The clasps of this partial denture 10 are both of a directly fitted type. When there are many missing teeth and many remaining teeth, it is often the case that a denture is provided with a plurality of conventional clasps, and three or more conventional clasps are used in many cases. However, as to the denture using both inventive and conventional clasps, as long as two or more teeth are remaining, a denture provided with one inventive clasp and one conventional clasp can readily be designed to be applicable to almost all cases.

When a denture provided with one inventive clasp and one conventional clasp was adapted to a user, there was a reply that comfortable feelings in use were obtained even at the portion provided with the conventional clasp. The conventional clasp may be made of cast alloy or wire. Further, the partial denture of the present invention may be attached to an implanted tooth. When a conventional wire clasp is used for the second fit, attachment and detachment of the wire clasp would be performed in the tooth axis direction.

Effects of Partial Dentures of First through Fourth Embodiments

Summary

The effects of the partial dentures of the embodiments are summarized as follows.

(E1) As to the Clasp (Compared to a Conventional Type):

(1) It is short, thin, and simple in shape.

(2) It is less likely broken.

(3) It hardly suffers deformation over a long-term use.

(4) It is unnecessary to change a fundamental shape of both arms upon manufacture.

(5) The amount of material used is small, which leads to a reduced cost (particularly advantageous when using Pt or Au).

(E2) As to the Clasped Tooth:

(1) It is unnecessary to especially count on a retaining force exerted by the undercut. That is, it is unnecessary to take into consideration the degree of protrusion of the clasped tooth. It is also unnecessary to take into consideration the tilting of the clasped tooth to the buccal side or the lingual side, although prosthesis may be necessary if the tilting toward the mesial or distal direction is large.

(2) The clasped tooth may be a vital or non-vital tooth. A tooth that rocks to a certain degree may also be used.

(3) A rest cavity is unnecessary (this means that a vital tooth does not need to endure tooth cutting).

(4) Adaptation to the surface of the clasped tooth is easier.

(5) No restraining force is exerted on the clasped tooth when the partial denture is stationary.

(6) Even if the partial denture moves at the time of occlusion, it moves in the direction not restrained by the arms, which prevents the load from being imposed on the clasped tooth.

(7) At the time of attachment or detachment of the partial denture, the clasped tooth would not likely suffer a force in the lateral direction (crossing the tooth axis).

(E3) As to the Partial Denture as a Whole:

In addition to be free from sense of foreign substance or sense of discomfort, it provides the following functions.

(1) Since the clasp rarely appears on the labial surface, it guarantees aesthetics.

(2) By bonding a white resin, on the extension of the resin of the denture base, to the holding arm on the labial surface (buccal surface), it is possible to hide the metal color.

(3) It is superior in retention and stability to the conventional partial denture.

(4) It is superior in masticatory ability to the conventional partial denture.

(5) Since it is attached and detached in one direction, it is easy for the user to attach and detach the denture. Still, it would not easily come off.

(6) The design of the partial denture is simplified. In particular, it is unnecessary to use a large number of retaining devices.

(7) It is easy to keep it clean, because of the simple shape of the clasp.

(8) In designing the partial denture, there is no big difference whether the arm is fitted to the mesial or distal side (while in the conventional type, the design would considerably be changed depending on the mesial or distal side).

(9) The size of the missing portion does not matter. In the extreme case, there is no problem with a single denture (one tooth is missing) or with 13 missing teeth (one tooth is remaining).

(10) The holding force of the denture is sufficiently guaranteed even if the denture base is reduced in area. For example, the base area can be reduced by hollowing out the resin base at the palate even in the case where only one tooth is remaining on the upper jaw. The palate uncovered with the denture base ensures a refreshed feeling as well as the sense of taste at meal time.

(11) It has a stress-breaking type retaining ability. Almost no burden is imposed on the teeth, or on the periodontal ligament.

(12) The inventive clasp described above would not cause penetration to the mucosa, and no force is exerted to cause sinkage of the partial denture (while in the conventional case, penetration of the partial denture would often take place).

(13) The state as if the partial denture were slightly floating is maintained, so that it feels light in weight, rather than heavy, when wearing the partial denture.

(14) Presence of a fit by the inventive clasp described above and a second fit of any form (by another inventive clasp, a conventional type clasp, a wall surface or the like) is sufficient to implement a partial denture. It is possible to provide a partial denture excellent in retaining force, stability, and the like.

(Fundamental Functions Required for Partial Denture)

Hereinafter, description will be made as to how the functions (r1) through (r4) of the rest described above are attained by the partial denture of the present invention. As to the function "(r1) to transmit the occlusal pressure applied to the partial denture to a clasped tooth", the occlusal pressure applied to the artificial tooth is received by the residual ridge mucosa. In the partial denture of the present invention, the arms are fitted to the root of the clasped tooth to softly embrace the tooth, so that the clasped tooth in itself does not need to receive the occlusal pressure applied to the artificial tooth. This means that, in the partial denture of the present invention, the above function (r1) of the rest becomes unnecessary. Conventionally, exertion of the function (r1) would have rather caused three-dimensional restraint on the clasped tooth, thereby increasing the burden thereon. In the partial denture of the present invention, as a result of removal of the rest, feelings in use, aesthetics and others are improved, and the clasp having a simple shape can readily be manufactured. As to the function "(r2) to prevent sinkage of the partial denture", the residual ridge mucosa can receive and handle the occlusal pressure applied to the artificial tooth as described above, so that sinkage of the partial tooth will not occur even if there is no rest.

Further, the functions "(r3) to hold the clasp in place" and "(r4) to suppress rocking of the partial denture" are achieved by the following configuration. In the partial denture of the present invention, the arms establish one fit as they are fitted to the root of the clasped tooth in a manner to softly hold the tooth in the arms. This fit, together with another fit by another clasp or the like in the partial denture, can achieve the functions (r3) and (r4).

As described above, since the rest is not provided, the pressure otherwise applied to the rest or the base point in the direction of sinkage is eliminated. Further, since the arms are fitted to the root of the clasped tooth in a manner to hold the tooth, the occlusal pressure applied to the artificial tooth is smoothly transmitted to the residual ridge mucosa directly beneath the artificial tooth without imposing a burden on the clasped tooth. Furthermore, with the two fits, one by the inventive arms and the other by another fitting portion, the functions (r3) and (r4) are implemented.

Now, description will be made as to how the functions (c1) and (c2) of the clasp described above are achieved by the partial denture of the present invention. As to the function "(c1) to prevent separation of the partial denture by a hook portion of the arm that extends from the top of the tooth crown to the undercut to act against the separation (lifting) force", the front-side arm and the back-side arm hold the root of the clasped tooth, i.e., they hold the clasped tooth at the undercut portion closer to the root side than the protruded portion, and accordingly, the contact of the two arms with the protruded portion exerts the separation-preventing force. Further, as to the function "(c2) to prevent rotation of the partial denture with an indirect retaining device as the fulcrum", the occlusal pressure is applied solely to the artificial tooth, because of no rest, and is exerted on the residual ridge mucosa in a plane, and thus, movement including rotation and displacement can be restricted. Furthermore, the mechanism (cooperation with the other fitting portion such as another clasp (or abutment of the wall surfaces)) for implementing the above-described functions (r3) and (r4) of the rest can be fulfilled here as well.

It will be understood, from the description of the partial denture of the present invention, that the (A1) supporting function against the occlusal pressure and the (A2) retaining function against the separation force, which are fundamental requisites for the partial denture, can be guaranteed without any problems. As a result, the functions of (A1) and (A2) prevent tilting of the partial denture. Further, as to the (A3) grasping function against the horizontal force applied to the denture, as already described in conjunction with the functions "(r3) to hold the clasp in place" and "(r4) to suppress rocking of the partial denture", it can be achieved with no problems through cooperation with the second fitting portion such as another clasp or the like of the partial denture. The two fitting portions described above are generally fitted to the corresponding clasped teeth in the direction crossing the tooth axis as described above, although there are exceptional cases.

It should be understood that the embodiments disclosed herein are illustrative and non-restrictive in every respect. The scope of the present invention is defined by the terms of the claims, rather than the description above, and is intended to include any modifications within the scope and meaning equivalent to the terms of the claims.

INDUSTRIAL APPLICABILITY

With the use of the partial denture of present invention, it is possible to provide a partial denture ensuring good feelings in use, exerting almost no burden on the clasped tooth, excellent in aesthetics, and easy to manufacture, which is expected to largely contribute to the field of the art.

The invention claimed is:

1. A partial denture having an artificial tooth, a denture base holding said artificial tooth, and a clasp fixed to said denture base, wherein
said clasp has a unitary construction and contains no rest and includes a back-side arm and a front-side arm, said front-side arm being shorter in length than said back-side arm, the back-side arm extending in a rearward bulging convex on a back side of a dentition-extended range of said denture base, the front-side arm extending in a forward bulging convex toward a front side of the dentition-extended range of said denture base, wherein said back-side arm and said front-side arm are branched from a fixed portion, with the entirety of said back-side arm and said front-side arm being in substantially the same plane as the entirety of said fixed portion and having a flat, substantially C-configuration, said back-side arm, said front-side arm and said fixed portion being formed by metal casting into said unitary construction said fixed portion being embedded in said denture base without cushioning materials intervening therebetween so that the clasp does not move relative to said denture base, and
said back-side arm and said front-side arm extend within a height range (S1) which is closer to a height of an extended plane of a top surface of said denture base than to a height of an extended plane of the top surface of the crown of said artificial tooth, so that substantially all of the C-shaped configuration is configured to be positioned on a root portion below a protruded side surface portion of the clasped tooth, whereby occlusal pressure is not applied on said clasped tooth and said occlusal pressure is smoothly transmitted from the artificial tooth to a residual ridge mucosa through said denture base.

2. The partial denture according to claim 1, wherein said partial denture is formed such that said front-side arm and said back-side arm of said clasp are configured to be fitted to a clasped tooth in a direction crossing a tooth axis, the clasped tooth being a remaining tooth to which said clasp is configured to be attached.

3. The partial denture according to claim 1, wherein said back-side arm and said front-side arm each have a surface for fitting to a tooth sidewall on a curved concave side.

4. The partial denture according to claim 1, further comprising a second clasp in addition to said clasp of said partial denture, the second clasp including a front-side arm curved in a forward bulging convex and a back-side arm curved in a rearward bulging convex, the second clasp including no rest.

5. The partial denture according to claim 4, wherein said second clasp is formed at an end of a major connector extending from the denture base on which said artificial tooth is fixed.

6. The partial denture according to claim 4, wherein said partial denture is formed such that the front-side arms and the back-side arms of said clasp and said second clasp are configured to be fitted to corresponding clasped teeth, respectively, in a direction crossing a tooth axis.

7. The partial denture of claim 4, wherein said clasp and said second clasp differ in opening direction from each other.

8. The partial denture according to claim 1, wherein said partial denture has a wall surface formed at an end of said denture base, said wall surface formed without a clasp other than said clasp of said partial denture.

9. The partial denture according to claim 1, wherein said arms of said clasp are formed of gold-platinum alloy.

10. The partial denture according to claim 1, wherein said back-side arm and said front-side arm are configured to be fitted to a tooth root portion of a clasped tooth exposed from a gum.

11. The partial denture according to claim 1, wherein said back-side arm and said front-side arm are adapted to restrict a moving direction of said artificial tooth to a direction along a tooth axis of said clasped tooth.

12. The partial denture of claim 1, wherein depressions are provided in the single fixed portion.

13. The partial denture of claim 1, wherein the back-side arm and the front-side arm have a width of not less than 1 mm up to about 3 mm.

14. The partial denture of claim 1, wherein free end portions of the back-side arm and the front-side arm are tapered.

15. The partial denture of claim 1, wherein the front-side arm of the clasp is configured to extend a distance of about 1 to 2 mm around a clasped tooth whereas the back-side arm is configured to extend about 70 to 90% around the width of the lingual surface of the clasped tooth.

16. The partial denture of claim 1, wherein the arms of the clasp are configured to make contact with a clasped tooth in the vicinity of the gingival margin and in substantially a horizontal state.

17. The partial denture according to claim 1, wherein a maximum distance across said front-side arm and said back-side arm is not less than an opening distance between the arms and not greater than 1.25 times the opening distance, the opening distance being a distance between a tip end of said front-side arm and a tip end of said back-side arm.

* * * * *